United States Patent
Achatz et al.

(10) Patent No.: US 10,697,031 B2
(45) Date of Patent: *Jun. 30, 2020

(54) COMBINED SYSTEM FOR PRODUCING STEEL AND METHOD FOR OPERATING THE COMBINED SYSTEM

(71) Applicant: ThyssenKrupp AG, Essen (DE)

(72) Inventors: Reinhold Achatz, Essen (DE); Jens Wagner, Frankfurt a.M. (DE); Markus Oles, Hattingen (DE); Peter Schmöle, Dortmund (DE); Ralph Kleinschmidt, Mülheim a.d.Ruhr (DE); Stefan Gehrmann, Dortmund (DE); Bärbel Kolbe, Witten (DE); Matthias Patrick Krüger, Herne (DE)

(73) Assignee: THYSSENKRUPP AG, Essen (DE)

( * ) Notice: Subject to any disclaimer, the term of this patent is extended or adjusted under 35 U.S.C. 154(b) by 166 days.

This patent is subject to a terminal disclaimer.

(21) Appl. No.: 15/102,518

(22) PCT Filed: Dec. 11, 2014

(86) PCT No.: PCT/EP2014/003316
§ 371 (c)(1),
(2) Date: Jun. 7, 2016

(87) PCT Pub. No.: WO2015/086150
PCT Pub. Date: Jun. 18, 2015

(65) Prior Publication Data
US 2016/0326605 A1   Nov. 10, 2016

(30) Foreign Application Priority Data
Dec. 12, 2013  (DE) .................. 10 2013 113 958

(51) Int. Cl.
  *C21B 5/06* (2006.01)
  *C21B 7/00* (2006.01)
  (Continued)

(52) U.S. Cl.
  CPC ............... *C21B 7/002* (2013.01); *C01B 3/12* (2013.01); *C01B 3/38* (2013.01); *C01B 3/56* (2013.01);
  (Continued)

(58) Field of Classification Search
  CPC ..................................................... C21C 5/285
  See application file for complete search history.

(56) References Cited

U.S. PATENT DOCUMENTS

2006/0027043 A1   2/2006  Zendejas-Martinez
2010/0317074 A1  12/2010  Simpson et al.
(Continued)

FOREIGN PATENT DOCUMENTS

CA   2751060 A1   8/2010
CN   1311825 A    9/2001
(Continued)

OTHER PUBLICATIONS

Canadian Application No. 2,930,451, Office Action dated Feb. 27, 2017, 5 pages.
(Continued)

*Primary Examiner* — Scott R Kastler
(74) *Attorney, Agent, or Firm* — Lathrop GPM LLP

(57) ABSTRACT

The invention relates to a plant complex for steel production comprising a blast furnace for producing pig iron, a converter steel mill for producing crude steel, a gas-conducting system for gases that occur when producing the pig iron and/or the crude steel, and a power-generating plant for electricity generation. The power-generating plant is designed as a gas-turbine power-generating plant or gas-
(Continued)

turbine and steam-turbine power-generating plant and is operated with a gas that comprises at least a partial amount of the blast-furnace top gas that occurs in the blast furnace and/or a partial amount of the converter gas. The plant complex additionally comprises a chemical plant and a biotechnological plant, the power-generating plant, the chemical plant and the biotechnological plant being arranged in a parallel setup with regard to the gas supply. The gas-conducting system comprises an operationally controllable gas-distributing device for dividing the streams of gas.

7 Claims, 2 Drawing Sheets

(51) Int. Cl.
| | |
|---|---|
| C21C 5/38 | (2006.01) |
| C01B 3/12 | (2006.01) |
| C01B 3/56 | (2006.01) |
| C01B 3/38 | (2006.01) |
| C01C 1/04 | (2006.01) |
| C07C 29/00 | (2006.01) |
| C10B 27/06 | (2006.01) |
| C12P 7/06 | (2006.01) |
| C12P 7/30 | (2006.01) |
| C21C 5/28 | (2006.01) |
| C25B 1/04 | (2006.01) |
| F01D 15/00 | (2006.01) |
| F02C 1/00 | (2006.01) |

(52) U.S. Cl.
CPC ............... *C01C 1/04* (2013.01); *C07C 29/00* (2013.01); *C10B 27/06* (2013.01); *C12P 7/06* (2013.01); *C12P 7/30* (2013.01); *C21B 5/06* (2013.01); *C21C 5/285* (2013.01); *C21C 5/38* (2013.01); *C25B 1/04* (2013.01); *F01D 15/00* (2013.01); *F02C 1/002* (2013.01); *C01B 2203/0233* (2013.01); *C01B 2203/0283* (2013.01); *C01B 2203/043* (2013.01); *C21B 2100/28* (2017.05); *C21B 2100/60* (2017.05); *C21B 2100/62* (2017.05); *Y02E 50/17* (2013.01); *Y02E 60/366* (2013.01); *Y02P 10/143* (2015.11); *Y02P 10/283* (2015.11); *Y02P 20/133* (2015.11)

(56) References Cited

U.S. PATENT DOCUMENTS

| | | | |
|---|---|---|---|
| 2011/0266726 A1* | 11/2011 | DePuy | C21B 5/00 266/140 |
| 2012/0226080 A1 | 9/2012 | Meyer-Pittroff | |
| 2014/0343339 A1* | 11/2014 | Schodel | C07C 41/01 585/639 |
| 2016/0326605 A1 | 11/2016 | Achatz et al. | |

FOREIGN PATENT DOCUMENTS

| | | |
|---|---|---|
| DE | 102011077819 A1 | 12/2012 |
| DE | 102013113913 A1 | 6/2015 |
| DE | 102013113921 A1 | 6/2015 |
| DE | 102013113942 A1 | 6/2015 |
| DE | 102013113950 A1 | 6/2015 |
| DE | 102013113958 A1 | 6/2015 |
| DE | 102013113980 A1 | 6/2015 |
| EP | 200880 A2 | 11/1986 |
| EP | 244551 A1 | 3/1990 |
| EP | 2543743 A1 | 1/2013 |
| EP | 2657215 A1 | 10/2013 |
| EP | 3080306 A1 | 10/2016 |
| FR | 2420568 A1 | 10/1979 |
| JP | 61275101 A | 12/1986 |
| JP | 2011225969 A | 11/2011 |
| RU | 2125613 C1 | 1/1999 |
| WO | 95/35393 A2 | 12/1995 |
| WO | 0005421 A1 | 2/2000 |
| WO | 2010136313 A1 | 12/2010 |
| WO | 2011018124 A1 | 2/2011 |
| WO | WO-2011116141 A2 * | 9/2011 ............ B82Y 30/00 |
| WO | 2012145910 A1 | 11/2012 |
| WO | 2012/174313 A2 | 12/2012 |
| WO | 2015086148 A1 | 6/2015 |
| WO | 2015086149 A1 | 6/2015 |
| WO | 2015086150 A1 | 6/2015 |
| WO | 2015086151 A1 | 6/2015 |
| WO | 2015086152 A1 | 6/2015 |
| WO | 2015086153 A1 | 6/2015 |
| WO | 2015086154 A1 | 6/2015 |

OTHER PUBLICATIONS

Chinese Application No. 201480067677.5, Office Action dated Jan. 11, 2018, 22 pages.
Canadian Application No. 2,930,451, Office Action dated Oct. 23, 2017, 4 pages.
Chinese Application No. 201480067677.5, Office Action dated May 2, 2017, 15 pages.
PCT Application No. PCT/EP2014/03316, Written Opinion, dated Jun. 18, 2015, 12 pages.
PCT Application No. PCT/EP2014/03316, International Search Report, dated Jun. 18, 2015, 4 pages.
Ghanbari et al. AIChE Journal, Optimal Design and Operation of a Steel Plant Integrated With a Polygeneration System, Oct. 2013, vol. 59, No. 10.
Third Party Observation dated Jul. 13, 2018.
Canadian Application No. 2,930,451, Office Action dated Apr. 3, 2019, six pages.
U.S. Appl. No. 15/102,142, Final Office Action dated Jan. 24, 2019, 14 pages.
Beijing Chorography Compilation Committee, Beijing Yearbook, Oct. 2013, Beijing Year Book Press, Beijing, China.

* cited by examiner

COMBINED SYSTEM FOR PRODUCING STEEL AND METHOD FOR OPERATING THE COMBINED SYSTEM

CROSS-REFERENCE TO RELATED APPLICATIONS

This application is the national phase of, and claims priority to, International Patent Application No. PCT/EP2014/003316, filed Dec. 11, 2014, which designated the U.S. and which claims priority to German Patent Application Number DE 10 2013 113 958.2, filed Dec. 12, 2013. These applications are each incorporated by reference herein in their entireties.

BACKGROUND

1. Field of the Invention

The invention relates to a plant complex for steel production and to a method for operating the plant complex.

2. Description of the Related Art

Pig iron is obtained in the blast furnace from iron ores, additives and also coke and other reducing agents such as coal, oil, gas, biomasses, recycled waste plastics or other substances containing carbon and/or hydrogen. CO, $CO_2$, hydrogen and water vapour inevitably occur as products of the reduction reactions. Apart from the aforementioned constituents, a blast-furnace top gas drawn off from the blast-furnace process often has a high content of nitrogen. The amount of gas and the composition of the blast-furnace top gas are dependent on the feedstock and the operating mode and are subject to fluctuations. Typically, however, blast-furnace top gas contains 35 to 60% by volume $N_2$, 20 to 30% by volume CO, 20 to 30% by volume $CO_2$ and 2 to 15% by volume $H_2$. Around 30 to 40% of the blast-furnace top gas produced in the production of the pig iron is generally used for heating up the hot air for the blast-furnace process in air heaters; the remaining amount of top gas may be used in other areas of the mill for heating purposes or for electricity generation.

In the converter steel mill, which is arranged downstream of the blast-furnace process, pig iron is converted into crude steel. By blowing oxygen onto liquid pig iron, troublesome impurities such as carbon, silicon, sulphur and phosphorus are removed. Since the oxidation processes cause an intense development of heat, scrap is often added in amounts of up to 25% with respect to the pig iron as a coolant. Furthermore, lime is added for forming slag and an alloying agent. A converter gas that has a high content of CO and also contains nitrogen, hydrogen and $CO_2$ is drawn off from the steel converter. A typical converter gas composition has 50 to 70% by volume CO, 10 to 20% by volume $N_2$, about 15% by volume $CO_2$ and about 2% by volume $H_2$. The converter gas is either burned off or, in the case of modern steel, captured and passed on to be used for providing energy.

The plant complex may optionally be operated in combination with a coking plant. In this case, the plant complex described at the beginning additionally comprises a coke-oven plant, in which coal is converted into coke by a coking process. In the coking of coal into coke, a coke-oven gas occurs, containing a high hydrogen content and considerable amounts of $CH_4$. Typically, coke-oven gas contains 55 to 70% by volume $H_2$, 20 to 30% by volume $CH_4$, 5 to 10% by volume $N_2$ and 5 to 10% by volume CO. In addition, the coke-oven gas has fractions of $CO_2$, $NH_3$ and $H_2S$. In practice, the coke-oven gas is used in various areas of the mill for heating purposes and in the power-generating process for electricity generation. In addition, it is known to use coke-oven gas together with blast-furnace top gas or with converter gas for producing syngases. According to a method known from WO 2010/136313 A1, coke-oven gas is separated into a hydrogen-rich gas stream and a residual gas stream containing $CH_4$ and CO, the residual gas stream being fed to the blast-furnace process and the hydrogen-rich gas stream being mixed with blast-furnace top gas and processed further into a syngas. It is known from EP 0 200 880 A2 to mix converter gas and coke-oven gas andse them as a syngas for methanol synthesis.

In an integrated metallurgical plant that is operated in combination with a coking plant, approximately 40 to 50% of the raw gases that occur as blast-furnace top gas, converter gas and coke-oven gas are used for chemical engineering processes. Approximately 50 to 60% of the gases produced are fed to the power-generating plant and used for electricity generation. The electricity produced in the power-generating plant covers the electricity demand for the production of pig iron and crude steel. Ideally, the energy balance is closed, so that, apart from iron ores and carbon in the form of coal and coke as sources of energy, no further energy input is necessary and, apart from crude steel and slag, no product leaves the plant complex.

SUMMARY

One object of the invention includes further improving the cost-effectiveness of the overall process and providing a plant complex with which it is possible to reduce the costs for steel production.

WRITTEN DESCRIPTION

Figure 1:
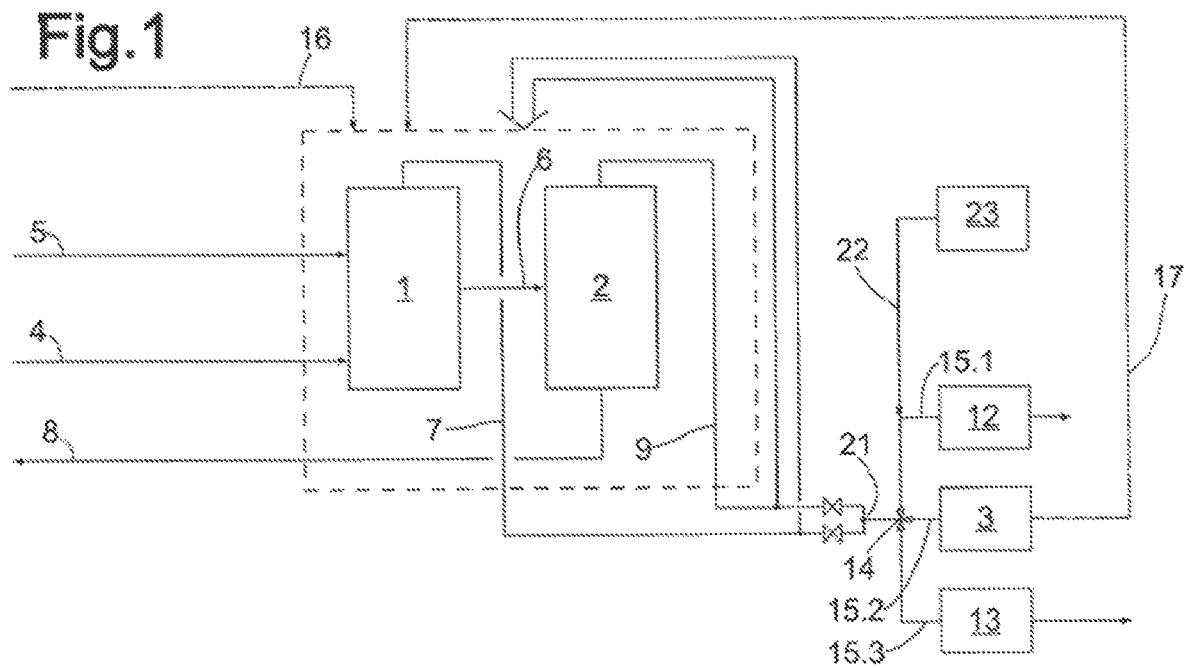
FIG. 1 shows a simplified block diagram of a plant complex for producing steel comprising a blast furnace for producing pig iron and a converter steel mill for producing crude steel, a power-generating plant, a chemical plant and a biotechnological plant.

The plant complex for steel production comprises a blast furnace for producing pig iron, a converter steel mill for producing crude steel, a gas-conducting system for gases that occur in the production of pig iron and/or in the production of crude steel, and also a power-generating plant for electricity generation. The power-generating plant is designed as a gas-turbine power-generating plant or gas-turbine and steam-turbine power-generating plant and is operated with a gas that comprises at least a partial amount of the blast-furnace top gas that occurs in the blast furnace when producing the pig iron and/or a partial amount of the converter gas that occurs in the converter steel mill.

Proceeding from a plant complex for steel production comprising a blast furnace for producing pig iron, a converter steel mill for producing crude steel, a gas-conducting system for gases that occur in the production of pig iron and/or the production of crude steel and a power-generating plant for electricity generation, according to the invention a chemical plant and a biotechnological plant are connected to the gas-conducting system, the power-generating plant, the chemical plant and the biotechnological plant being arranged in a parallel setup with regard to the gas supply. According to the invention, the gas-conducting system comprises an operationally controllable gas-distributing device for dividing the streams of gas that are fed to the power-generating plant, the chemical plant and the biotechnological plant.

The subject of the invention is also a method for operating a plant complex that has a blast furnace for producing pig iron, a converter steel mill, a chemical plant, a biotechnological plant and a power-generating plant. According to the method according to one embodiment of the invention, at least a partial amount of the blast-furnace top gas that occurs in the production of pig iron in the blast furnace and/or a partial amount of the converter gas that occurs in the production of crude steel is used as a useful gas for operating the power-generating plant, the chemical plant and the biotechnological plant. A first partial stream of the useful gas is fed to the chemical plant and used after a gas-conditioning operation as syngas for producing chemical products. A second partial stream of the useful gas is used in the power-generating plant for electricity generation. A third partial stream of the useful gas is fed to the biotechnological plant and used for biochemical processes. The third partial stream may be used for biochemical processes with or without gas conditioning. In the case of a change of the gas stream fed to the power-generating plant, the second partial stream and the third partial stream of the useful gas are changed alternately, so that the chemical plant can be operated with a partial stream of the useful gas that is subject to less operational fluctuations than the partial stream of useful gas that is used in the biotechnological plant. The third partial stream of useful gas is expediently controlled in such a way that the first partial stream of useful gas, used in the chemical plant, is operated constantly with a range of fluctuation of ±20%.

In the chemical plant, chemical products are produced from syngases that respectively contain the components of the reactant. Chemical products may be for example ammonia or methanol or else other hydrocarbon compounds.

A biotechnological plant is taken to mean a plant for the fermentation of syngas that contains CO and $H_2$ as the main constituents. Hydrocarbon compounds, for example ethanol, acetone and the like, can likewise be produced from this syngas. However, the hydrogen fraction in this case originates substantially from water, which is used as a medium in the fermentation. Therefore, a gas which has a high proportion of CO is required for producing the syngas. Converter gas or a mixed gas comprising converter gas and blast-furnace top gas is preferably used.

The partial stream of useful gas that is used in the power-generating plant for electricity generation is subject to considerable operational fluctuations. The electricity produced by the power-generating plant covers part of the electricity demand of the plant complex. In addition, external electricity is obtained, preferably obtained completely or at least partially from renewable energy and originating for example from wind turbine generator plants, solar plants, geothermal power-generating plants, hydroelectric power-generating plants, tidal power-generating plants and the like. To achieve operation of the plant complex that is as cost-effective as possible, the operation of the power-generating plant is cut back if external electricity is available in a sufficient amount and at favourable prices. If electricity from regenerative sources is not available to a sufficient extent or external electricity has a higher price than electricity that can be produced in the power-generating plant, the output of the power-generating plant is increased and most of the useful gas is used in the power-generating process for electricity generation. The proportion of the useful gas that can be used as syngas for producing chemical products is therefore subject as a result to considerable operational fluctuations, which are predetermined by the operation of the power-generating plant.

The dynamic control of a chemical plant under load changes is technically complex. The problem that a chemical plant operated in combination with a power-generating plant cannot react sufficiently flexibly to load changes of the power-generating plant is solved according to the invention by initially only the product output of the biotechnological plant being adapted when there is a load change of the power-generating plant and by the partial stream of useful gas that is intended for the biotechnological plant and the partial stream of useful gas that is used in the power-generating plant being changed alternately, so that the chemical plant can be operated with a partial stream of the useful gas that is subject to significantly less operational fluctuations than the partial stream of useful gas that is used in the biotechnological plant. The teaching according to the invention thereby makes use of the fact that a biotechnological plant is much more flexible with regard to load changes in comparison with a chemical plant.

According to a preferred embodiment of the invention, the plant complex additionally comprises a coke-oven plant. If the production of pig iron and the production of crude steel are operated in combination with a coking plant, a partial amount of the blast-furnace top gas that occurs in the production of pig iron and/or a partial amount of the converter gas that occurs in the converter steel mill may be mixed with a partial amount of the coke-oven gas that occurs in the coke-oven plant and the mixed gas may be used as a useful gas. A mixture of coke-oven gas and blast-furnace top gas or a mixed gas comprising coke-oven gas, converter gas and blast-furnace top gas may be used for producing a syngas, for example for ammonia synthesis. A mixed gas comprising coke-oven gas and converter gas or a mixed gas comprising coke-oven gas, converter gas and blast-furnace top gas is suitable for producing hydrocarbon compounds.

Converter gas, blast-furnace top gas or a mixed gas comprising these two gas components is preferably used for operating the biotechnological plant. The coke-oven gas is not suitable or less suitable for the biotechnical process. To this extent it may be expedient to use in the chemical plant and in the biotechnological plant streams of useful gas that differ with regard to their composition.

The raw gases—coke-oven gas, converter gas and/or blast-furnace top gas—may be conditioned individually or in combination as a mixed gas and then used as a syngas in the chemical plant and the biotechnological plant. The conditioning of coke-oven gas in particular comprises a cleaning of the gas to separate out troublesome contents, in particular tar, sulphur and sulphur compounds, aromatic hydrocarbons (BTX) and high-boiling hydrocarbons. A gas-conditioning operation is also necessary for the production of the syngas. In the course of the gas conditioning, the proportion of the components CO, $CO_2$ and $H_2$ within the raw gas is changed. The gas conditioning comprises for example pressure swing adsorption for separating out and enriching $H_2$ and/or a water-gas-shift reaction for converting CO into hydrogen and/or a steam reformer for converting the $CH_4$ fraction into CO and hydrogen in the coke-oven gas.

The first partial stream of the useful gas, used in the chemical plant, may be enriched with hydrogen that is produced in an additionally connected plant. The production of hydrogen preferably takes place by electrolysis of water, it being possible for the electrolysis of water to be operated with electrical power from regenerative sources. Oxygen is also produced in the electrolysis of water, and can be used in the blast furnace for producing pig iron and/or in the converter steel mill for producing crude steel.

The invention also covers the use of a chemical plant in combination with a biotechnological plant for coupling to a metallurgical plant.

The plant complex for producing steel that is represented in FIG. 1 comprises a blast furnace 1 for producing pig iron, a converter steel mill 2 for producing crude steel and a power-generating plant 3 for electricity generation.

In the blast furnace 1, pig iron 6 is obtained substantially from iron ore 4 and reducing agents 5, in particular coke and coal. Reduction reactions cause the production of a blast-furnace top gas 7, which contains nitrogen, CO and $CO_2$ as the main constituents and a small proportion of $H_2$. In the converter steel mill 2 that is arranged downstream of the blast-furnace process, pig iron 6 is converted into crude steel 8. By blowing oxygen onto the liquid pig iron, troublesome impurities, in particular carbon, silicon and phosphorus, are removed. For cooling, scrap may be added in amounts of up to 25% with respect to the amount of pig iron. Furthermore, lime is added for forming slag and an alloying agent. At the top of the converter, a converter gas 9 that has a very high proportion of CO is drawn off.

The power-generating plant 3 is designed as a gas-turbine power-generating plant or gas-turbine and steam-turbine power-generating plant and is operated with a gas that comprises at least a partial amount of the blast-furnace top gas 7 that occurs in the production of pig iron in the blast furnace 1 and a partial amount of the converter gas 9 that occurs in the converter steel mill 2. A gas-conducting system is provided for carrying the gases.

According to the overall balance represented in FIG. 1, carbon is fed to the plant complex as a reducing agent 5 in the form of coal and coke and also iron ore 4. Occurring as products are crude steel 8 and raw gases 7 and 9, which differ in amount, composition, calorific value and purity and are used again at various points in the plant complex. In an overall consideration, 40 to 50%, usually approximately 45%, of the raw gases 7 and 9 are returned again into the metallurgical process for producing pig iron or producing crude steel. Between 50 and 60%, usually approximately 55%, of the raw gases 7 and 9 can be used for operating the power-generating plant 3.

According to the representation in FIG. 1, the plant complex additionally comprises a chemical plant 12 and a biotechnological plant 13, the power-generating plant 3, the chemical plant 12 and the biotechnological plant 13 being arranged in a parallel setup with regard to the gas supply. The gas-conducting system has an operationally controllable gas-distributing device 14 for dividing the streams of gas that are fed to the power-generating plant 3, the chemical plant 12 and the biotechnological plant 13. Provided upstream of the gas-distributing device 14 in the direction of flow may be a mixing device 21, for producing a mixed gas consisting of blast-furnace top gas 7 and converter gas 9.

The blast-furnace top gas 7 and the converter gas 9 may be combined with one another in any way desired. The combination of gas streams 7, 9 depends on the desired syngas or the product that is to be produced in the chemical plant 12. It is also within the scope of the invention that the biotechnological plant 13 is fed a stream of gas of a composition that differs from the gas composition used in the chemical plant 12.

In the case of the plant complex represented in FIG. 1, at least a partial amount of the blast-furnace top gas 7 that occurs in the production of pig iron in the blast furnace 3 and/or a partial amount of the converter gas 9 that occurs in the production of crude steel is used for operating the power-generating plant 3, the chemical plant 12 and the biotechnological plant 13. A first partial stream 15.1 of the useful gas is fed to the chemical plant 12 and used after a gas-conditioning operation as syngas for producing chemical products. A second partial stream 15.2 of the useful gas is used in the power-generating plant 3 for electricity generation. A third partial stream 15.3 of the useful gas is fed to the biotechnological plant 13 and used for biochemical processes.

Externally obtained electricity 16 and power-generating plant electricity 17, which is produced by the power-generating plant 3 of the plant complex, are used to cover the electricity demand of the plant complex. The externally obtained electricity 16 is preferably obtained completely or at least partially from renewable energy and originates for example from wind turbine generator plants, solar plants, hydroelectric power-generating plants and the like. To achieve operation of the plant complex that is as cost-effective as possible, electricity is bought in as external electricity 16 at times of low electricity prices and the power-generating process for supplying electricity is cut back. At times of high electricity prices, the partial stream 15.2 of the useful gas that is used in the power-generating plant 3 for producing electricity is increased.

In the case of a change of the gas stream fed to the power-generating plant 3, the second partial stream 15.2 and the third partial stream 15.3 of the useful gas are changed alternately, so that the chemical plant 12 can be operated with a partial stream 15.1 of the useful gas that is subject to less operational fluctuations than the partial stream of useful gas 15.3 that is used in the biotechnological plant 13. The third partial stream of useful gas 15.3 is expediently controlled in such a way that the first partial stream of useful gas 15.1, used in the chemical plant 12, is operated constantly with a range of fluctuation of ±20%.

Figure 2:
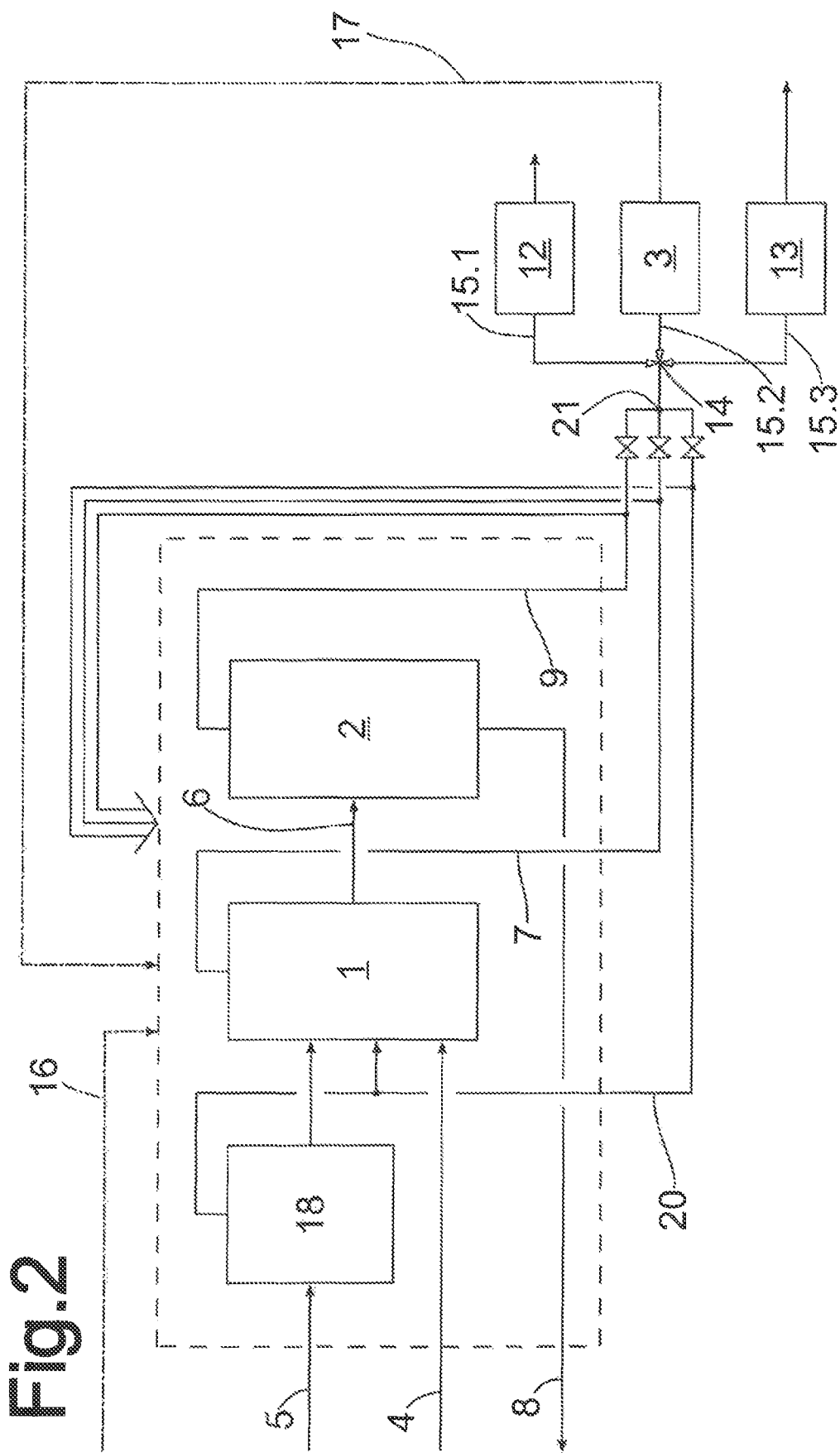
FIG. 2 shows a simplified block diagram of a plant complex which comprises in addition to a blast furnace for producing pig iron, a converter steel mill for producing crude steel, a power-generating plant, a chemical plant and a biotechnological plant also a coke-oven plant.

In the exemplary embodiment of FIG. 2, the plant complex additionally comprises a coke-oven plant 18. In the coking of coal into coke, coke-oven gas 20 occurs, containing a high proportion of hydrogen and $CH_4$. Parts of the coke-oven gas 20 may be used for the heating of the air heaters in the blast furnace 1. The gas-conducting system includes a gas distribution for the coke-oven gas 20. Provided upstream of the gas-distributing device 14 in the direction of flow there may be a mixing device 21, for producing a mixed gas consisting of blast-furnace top gas 7, converter gas 9 and coke-oven gas 20.

The blast-furnace top gas 7, the converter gas 9 and the coke-oven gas 20 may be combined with one another in any way desired. The combination of gas streams 7, 9, 20 depends on the desired syngas or the product that is to be produced in the chemical plant 12. It is also within the scope of the invention that the biotechnological plant 13 is fed a stream of gas of a composition that differs from the gas composition used in the chemical plant 12.

Also in the case of the plant concept represented in FIG. 2, a first partial stream 15.1 of the useful gas is fed to the chemical plant 12 and used after a gas-conditioning operation as syngas for producing chemical products. A second partial stream 15.2 of the useful gas is used in the power-generating plant 3 for producing electricity. A third partial stream 15.3 of the useful gas is fed to the biotechnological plant 13 and used for biochemical processes. In the case of a change of the gas stream fed to the power-generating plant 3, the second partial stream 15.2 and the third partial stream 15.3 of the useful gas are changed alternately, so that the chemical plant 12 can be operated with a partial stream 15.1 of the useful gas that is subject to less operational fluctuations than the partial stream of useful gas 15.3 that is used in the biotechnological plant.

The first partial stream 15.1 of the useful gas, used in the chemical plant 12, may also be enriched with hydrogen 22 that is produced in an additionally connected plant for producing hydrogen 23 that is optionally provided.

Many different arrangements of the described invention are possible without departing from the spirit and scope of the present invention. Embodiments of the present invention are described herein with the intent to be illustrative rather than restrictive. Alternative embodiments will become apparent to those skilled in the art that do not depart from its scope. A skilled artisan may develop alternative means of implementing the disclosed improvements without departing from the scope of the present invention.

Further, it will be understood that certain features and subcombinations are of utility and may be employed without reference to other features and subcombinations and are contemplated within the scope of the claims. Not all steps listed in the various figures and description need to be carried out in the specific order described. The description should not be restricted to the specific described embodiments.

The invention claimed is:

1. A plant complex for producing steel, comprising:
a blast furnace for producing pig iron;
a converter steel mill for producing crude steel;
a gas-conducting system for transporting one or more streams of gases that occur in the production of pig iron and crude steel; and
a power-generating plant for electricity generation, the power-generating plant being designed as a gas-turbine power-generating plant or gas-turbine and steam-turbine power generating plant and being operated with a gas supply that comprises at least a partial amount of one of a blast-furnace top gas that occurs in the production of pig iron in the blast furnace, and a converter gas that occurs in the converter steel mill;
wherein:
a chemical plant and a biotechnological plant are connected to the gas-conducting system;
the power-generating plant, the chemical plant, and the biotechnological plant are arranged in a parallel setup, wherein each of the power-generating plant, the chemical plant, and the biotechnological plant receive a partial stream of gas diverted from the gas supply such that the power-generating plant, the chemical plant, and the biotechnological plant are operated simultaneously in parallel; and
the gas-conducting system comprises an operationally adjustable gas-distributing device for dividing and controlling the gas supply that is fed to the power-generating plant, the chemical plant, and the biotechnological plant, wherein the gas-distributing device is adjusted when a price for externally obtained electricity reaches a predetermined threshold;
the biotechnological plant produces a hydrocarbon compound by a fermentation of a syngas comprising CO and $H_2$ as main constituents; and
the gas supply to the chemical plant remains substantially constant during operation of the plant.

2. The plant complex according to claim 1, wherein the plant complex further comprises a coke-oven plant, and wherein the gas-conducting system includes a gas distribution for coke-oven gas that occurs in a coking process in the coke-oven plant.

3. The plant complex according to claim 1, wherein the gas-conducting system has, upstream of the gas-distributing device in the direction of flow, a mixing device for producing a mixed gas consisting of at least one of the blast-furnace top gas, the converter gas, and the coke-oven gas.

4. The plant complex according to claim 1, wherein the plant complex additionally has a plant for producing hydrogen, which is connected to the gas-conducting system by a hydrogen-carrying line.

5. A plant complex for producing steel, comprising:
a biotechnological plant coupled to a metallurgical plant, the metallurgical plant comprising at least one blast furnace for producing pig iron, a converter steel mill, and a gas-operated power-generating plant for electricity generation, the gas-operated power-generating plant being designed as a gas-turbine power-generating plant or gas-turbine and steam-turbine power-generating plant;
wherein:
a partial amount of at least one of a blast-furnace top that occurs in the production of pig iron and a converter gas that occurs in the production of crude steel is used as a useful gas for operating the power-generating plant, the chemical plant, and the biotechnological plant;
the chemical plant, the biotechnological plant, and the power-generating plant are connected in parallel with respect to the carrying of gas such that the chemical plant, the biotechnological plant, and the power-generating plant are operated simultaneously;
the biotechnological plant produces a hydrocarbon compound by a fermentation of a syngas comprising CO and $H_2$ as main constituents; and
at least the partial streams of the useful gas that are fed to the biotechnological plant and the power-generating plant can be controlled separately via a gas-distributing device, wherein the partial streams of the useful gas are adjusted when a price for externally obtained electricity reaches a predetermined threshold.

6. The plant complex of claim 1, wherein the gas supply to the chemical plant is within ±20% of a predetermined chemical gas supply value.

7. The plant complex of claim 5, wherein the syngas is the converter gas, or a mixed gas comprising the converter gas and the blast furnace top gas.

* * * * *